(12) United States Patent
Rudolf

(10) Patent No.: US 12,031,954 B2
(45) Date of Patent: Jul. 9, 2024

(54) FORCE SENSING STRAINS IN SOFT MATERIALS FOR MILLISECOND-SCALE BLAST AND IMPACT CHARACTERIZATION

(71) Applicant: The Government of the United States of America, as represented by the Secretary of the Navy, Arlington, VA (US)

(72) Inventor: Christopher Rudolf, Washington, DC (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 0 days.

(21) Appl. No.: 17/184,030

(22) Filed: Feb. 24, 2021

(65) Prior Publication Data

US 2021/0262909 A1 Aug. 26, 2021

Related U.S. Application Data

(60) Provisional application No. 62/980,810, filed on Feb. 24, 2020.

(51) Int. Cl.
*G01N 3/30* (2006.01)
*G01N 3/06* (2006.01)

(52) U.S. Cl.
CPC .............. *G01N 3/30* (2013.01); *G01N 3/066* (2013.01); *G01N 2203/001* (2013.01)

(58) Field of Classification Search
CPC .. G01N 3/30; G01N 3/32; G01N 3/40; G01N 3/48; G01N 3/52; G01L 1/22
See application file for complete search history.

(56) References Cited

U.S. PATENT DOCUMENTS

| | | | |
|---|---|---|---|
| 7,024,922 B1 * | 4/2006 | Nakagawa | G01N 3/30 73/54.39 |
| 8,725,449 B2 * | 5/2014 | Roberts | G01R 33/0064 600/12 |
| 9,797,791 B2 * | 10/2017 | Vogt | G01L 1/02 |
| 9,841,331 B2 * | 12/2017 | Wood | A61B 5/1036 |
| 9,867,414 B2 * | 1/2018 | Thomas | G01M 7/08 |
| 2015/0088043 A1 * | 3/2015 | Goldfield | A61F 5/01 602/6 |
| 2020/0271445 A1 * | 8/2020 | Zhou | B82Y 30/00 |

* cited by examiner

*Primary Examiner* — Erika J. Villaluna
(74) *Attorney, Agent, or Firm* — US Naval Research Laboratory; Suresh Koshy

(57) ABSTRACT

A method of measuring millisecond-scale blast and impact characterization in soft materials includes embedding one or more sensors in soft material, wherein the one or more sensors have mechanical properties approximately matching the soft material; applying a constant current to the one or more sensors; subjecting the soft material to a shock or impact event; measuring a response as a change in voltage; and converting the measured voltage to strain or pressure.

8 Claims, 5 Drawing Sheets

FORCE SENSING STRAINS IN SOFT MATERIALS FOR MILLISECOND-SCALE BLAST AND IMPACT CHARACTERIZATION

RELATED APPLICATIONS

This application claims the benefit of U.S. Provisional Application No. 62/980,810 filed Feb. 24, 2020, which is hereby incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, DC 20375, USA; +1.202.767.7230; techtran@nrl.navy.mil, referencing NC 112519.

FIELD OF INVENTION

The present invention relates generally to strain measurement, and more particularly to dynamic, high-rate measurement (e.g., blast and impact events) related to biological systems.

BACKGROUND

Traumatic brain injury (TBI) and bodily tissue damage is a known consequence of military combat and contact sports, but the mechanisms that result in injury are not well understood for all types of high rate forces. Obvious limitations in human testing have led to the use of bio-surrogate or biofidelic model testing where the surrogate materials and components are tailored to mimic the response of human tissue. Conventional bio-surrogate model testing incorporates pressure sensors and accelerometers at strategically placed locations typically on human surrogate chest and head structures. However, there is currently no commercially available method for measuring strains within the surrogate tissue and the only method known presently utilizes a dispersion of metal beads in the surrogate tissue and a high speed x-ray system to measure deformation strains. This method is highly experimental, expensive, and is not amenable to field testing. There is a need for implantable strain sensors for measuring deformation in soft materials in order to enable surrogate model testing metrics with direct links to brain injury/trauma.

SUMMARY OF INVENTION

Therefore, described herein is a new process that utilizes a soft material with embedded resistive, liquid metal sensors for quantifying high rate strains in soft materials. The new process allows 1) an impedance-matched sensor to biofidelic human tissue for accuracy and unimpeded movement; 2) a capability to operate over small to moderately large (>20%) strains in materials experiencing complex deformations at dynamic rates (millisecond blast and impact events); 3) the ability to measure deformations in visually-obscured gel materials.

According to one aspect of the invention, a method of measuring millisecond-scale blast and impact characterization in soft materials includes embedding one or more sensors in soft material, wherein the one or more sensors have mechanical properties approximately matching the soft material; applying a constant current to the one or more sensors; subjecting the soft material to a shock or impact event; measuring a response as a change in voltage; and converting the measured voltage to strain.

Optionally, the one or more sensors are three sensors configured parallel to each other and successively rotationally offset by 45 degrees to measure strain in two dimensions.

Optionally, the one or more sensors are six sensors configured in a cubic orientation and configured to measure strain in three dimensions.

Optionally, the one or more sensors comprise a elastomeric material having a serpentine channel therein, the serpentine channel being filled with a liquid metal.

Optionally, the liquid metal is eutectic-gallium-indium.

Optionally, the elastomeric material is silicone.

Optionally, the elastomeric material is EcoFlex 00-30.

Optionally, the method includes lead wires inserted into the serpentine channel and connecting the wires to a data acquisition and control system by Kelvin clips.

Optionally, the shock or impact event is on the order of millisecond-scale pulse widths.

According to another aspect of the invention, a method of measuring wave speeds and pressure changes as a wave propagates through soft material includes embedding multiple sensors through a length of the soft material at known distances; applying a constant current to the sensors; subjecting the soft material to a shock or impact event; measuring a voltage and time at each sensor; and converting the measured voltage to pressure and using time of flight for calculating wave speed.

Optionally, the sensors comprise an elastomeric material having a spiral channel therein, the spiral channel being filled with liquid metal.

Optionally, the liquid metal is eutectic-gallium-indium.

Optionally, the elastomeric material is silicone.

Optionally, the elastomeric material is EcoFlex 00-30.

Optionally, the method includes lead wires inserted into the spiral channel and connected to a data acquisition and control system by Kelvin clips.

Optionally, the shock or impact event is performed at dynamic, injury relevant rates.

Optionally, the shock or impact event is on the order of millisecond-scale pulse widths.

The foregoing and other features of the invention are hereinafter described in greater detail with reference to the accompanying drawings.

DETAILED DESCRIPTION

The use of liquid metal in elastomer strain gauges has previously been used in the fields of soft robotics, wearable computing, and biomedical applications. These applications have a need for quantification of stretching-contraction deformations, require a device that can conform to the movements of the component under test (i.e. large strains), while also having a low stiffness so as not to hinder the measured system's movement. The benefit of the liquid metal in elastomer gauges is that they are much less stiff than traditional resistive metal strain gauges and can measure much larger strains (up to 250% compared to <1% of resistive metal gauges). Conductive liquid metals are limited in their deformability only by the mechanical properties of the substrate that encase them. However, they have relatively low resistance that results in noisy signals and have heretofore been focused on large strain as opposed to high rate measurements. Additionally, they exhibit nonlinear responses with large hysteresis over their operating range. Use of these liquid metal, elastomer sensors in the characterization of high rate deformations overcomes the otherwise observed hysteresis as a result of the short time scales and displacements involved in bio-surrogate tissue response.

Exemplary processes utilize elastomer-encased liquid metal sensors embedded in biofidelic soft materials and a high rate data acquisition system to enable force/deformation sensing in soft materials for millisecond-scale blast and impact characterization.

Figure 1:
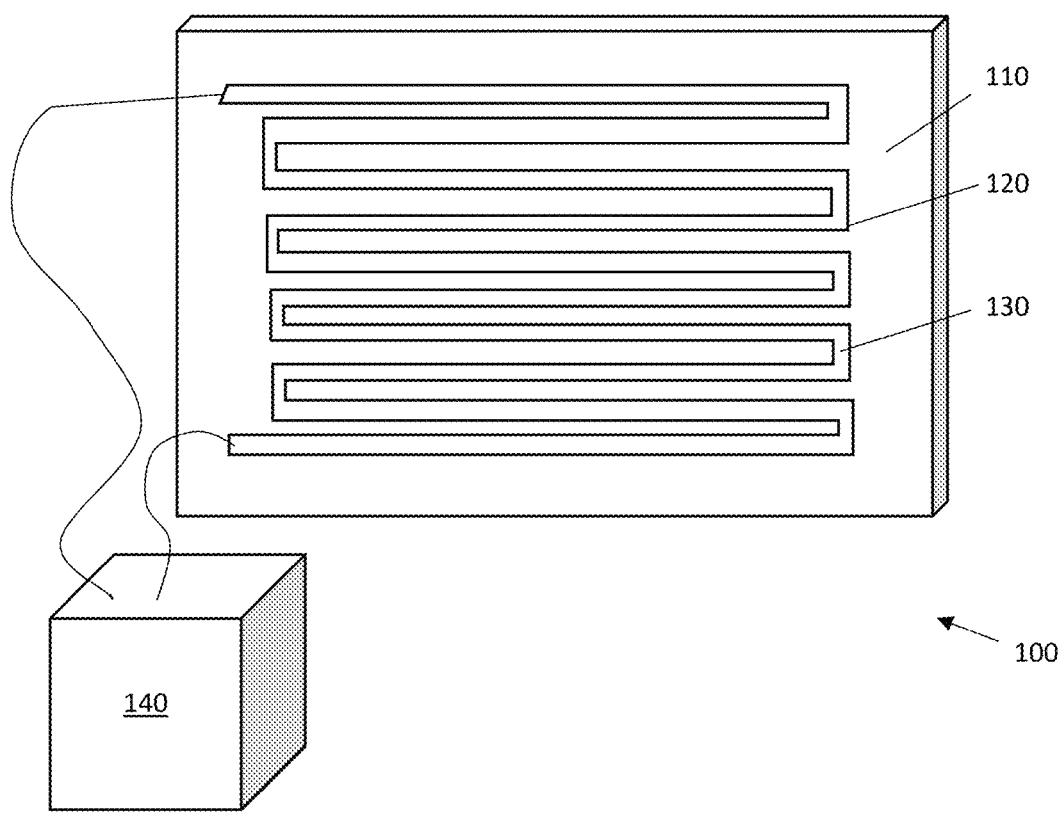
FIG. 1 shows an exemplary strain gage with an elastomeric body containing a liquid metal in a serpentine channel.

Also described herein is an exemplary fabricated force/displacement sensor comprised of a soft elastomer material with embedded channels filled with liquid metal, an experiment-appropriate mount, a data acquisition system, and a system to provide incident force. The sensor (FIG. 1) acts as a conventional strain-gauge where its resistance varies with applied force. As shown in FIG. 1, an exemplary system 100 includes a biofidelic soft material 110 having a serpentine channel 120 therein. This channel may take any appropriate form, but is preferably a rectilinear (shown) for strain measurements or spiral pattern for pressure measurements. The channel is filled with a conductive fluid, preferably a liquid metal 130. A constant current is applied across the length of the channel and the change in voltage (as a result of a change in resistance from deformation) is measured to infer a strain or pressure in the system being measured. The sensor may be connected to a data acquisition and control system (DACS) (e.g., National Instruments PXI system running a Labview program) 140. The DACS supplies a constant current through the gauge while simultaneously acquiring the voltage measurements. The change in voltage is directly a result of the changing resistance of the gauge due to deformation. Calibration can be performed prior to sensor use to determine the gauge factor, thereby enabling accurate strain measurements from the resultant change in measured voltage. Calibration can be performed by deforming the sensors to controlled, known displacements and recording the change in measured voltage.

Figure 2:
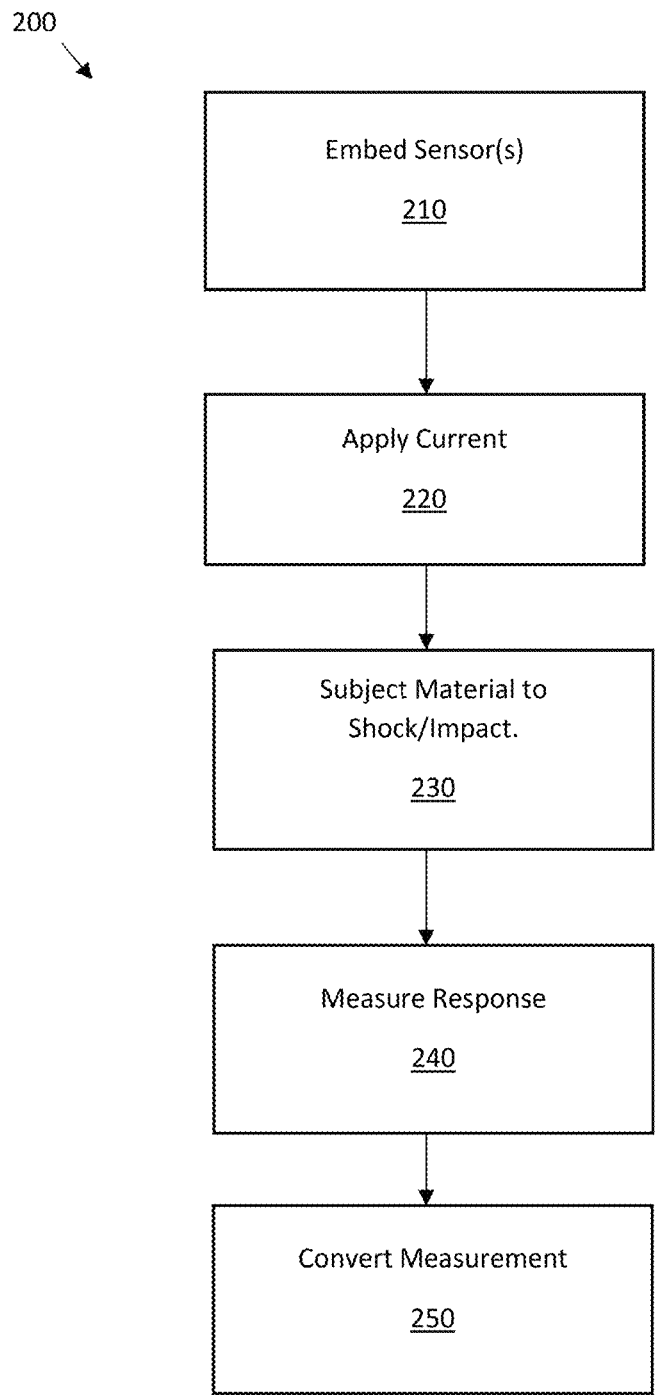
FIG. 2 shows a flow diagram of an exemplary method of measuring strain in a soft material.

This process 200 is illustrated in FIG. 2. At block 210, one or more sensors are embedded in soft material. At block 220, a constant current is applied to the one or more sensors. At block 230, the soft material is subjected to a shock or impact event. At block 240, a response is measured as a change in voltage. At block 250, the measured voltage is converted to strain.

The calibrated sensor may be embedded in a bio-surrogate soft material (typically gels/other elastomers) and mounted in a test-specific housing. The gauges can be oriented for the desired quantification and multiple gauges can be utilized for 2D conformal and 3D volumetric strain measurements.

Figure 3:
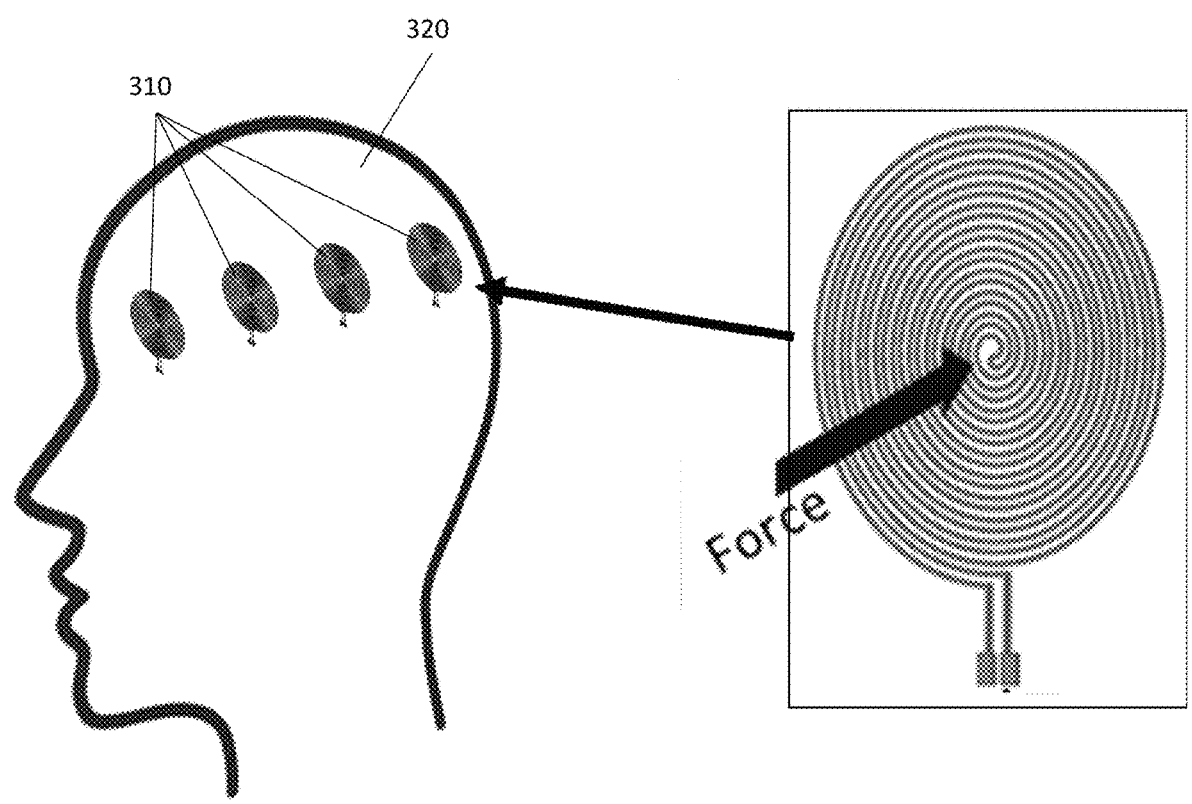
FIG. 3 shows a schematic diagram of an exemplary system to measure wave propagation through soft tissue.
Figure 4:
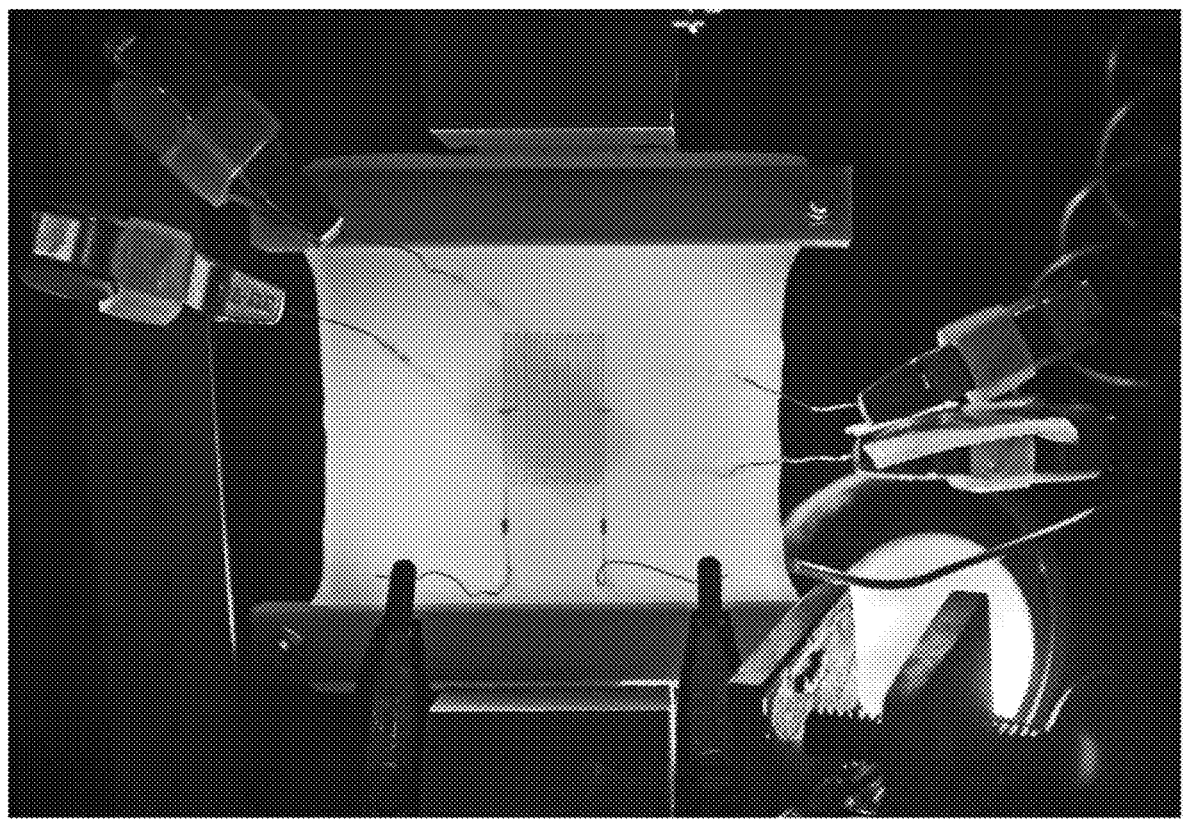
FIG. 4 shows a photo of an embodiment of the invention reduced to practice and including three sensors configured parallel to each other and successively rotationally offset by 45 degrees.
Figure 5:
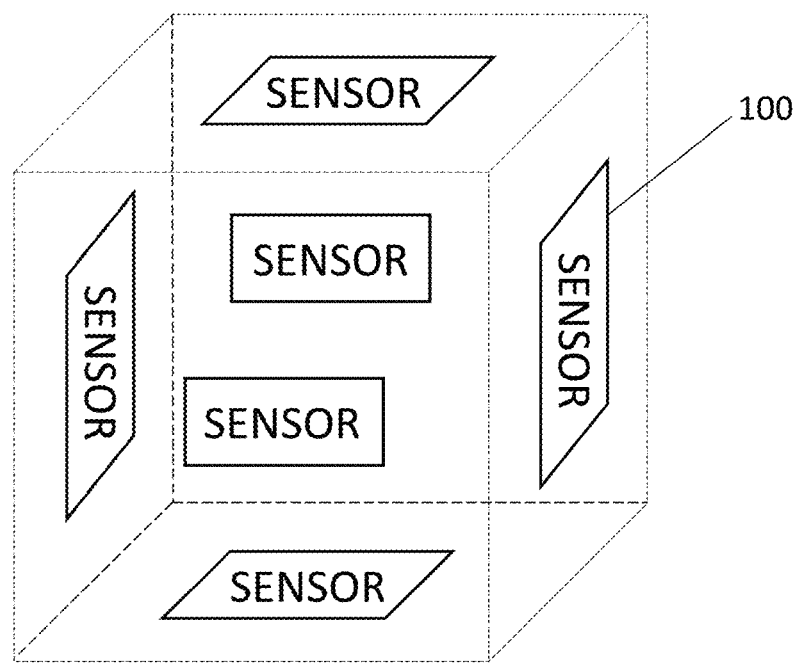
FIG. 5 shows a perspective view of an embodiment of the invention including six sensors configured in a cubic orientation.

Referring to FIG. 3, a plurality of sensors 310 can be distributed through a soft material 320 in order to measure wave speeds and pressure changes as a wave propagates through the soft material. The plurality of embedded sensors should be distributed at known distances and have a constant current applied to them, as described above, and are preferably oriented perpendicular to the direction of wave propagation. Next, the soft material is subjected to a shock or impact event, and the voltage response of the sensors can be measured and converted into pressure readings over time. This time data can then be used to calculate wave speed using time of flight calculations with the known distance between sensors.

Initial prototype tests were performed by high rate (~8 msec), injury relevant blast event loading using a shocktube system with the incident blast perpendicular to the length of the face of the sensor as well as by impact event loading using a linear shock table with the impact force parallel with the sensor face in both primary (in the direction of the length of the channels) and off-axis (perpendicular to the length of the channels) directions. Initial tests prove an orientation dependence of the sensors with a voltage response recorded for all primary axis measurements and practically no response to off-axis forces. This orientation dependence increases measurement accuracy by removing possible reflection responses.

It is known that straining of brain tissue leads to injury (diffuse axonal injury) but there is no currently available method for quantification. Exemplary embodiments consistent with the present invention enable this ability and are capable of force and deformation sensing of strains in soft bio-surrogate model testing during high rate blast and impact events. The use of sensors comprised of soft elastomers with embedded liquid metal conductive elements provide for impedance-matching to bio-surrogate materials enabling the ability to measure deformations in visually-obscured soft materials. As a point of relevance, the pressures/accelerations tested with the prototype have previously been shown to result in neuronal cell culture metabolisms. The sensors have shown an orientation dependence to allow for accurate strain response of desired locations relative to the impinging force event. Using these sensors during bio-surrogate ballistic impact and helmet testing can enhance the protection capability quantification resulting in better protection against injury.

Exemplary embodiments are customizable for desired applications. The elastomer utilized for the sensor is chosen for impedance-matching to the mechanical properties of the material of study. The sensor size can be easily scaled using various fabrication methods such as casting, laser ablation of embedded channels, and photolithography, enabling quantification from mm to μm deformation scales. The design of the gauge's liquid metal resistive element (i.e. serpentine channels, spiral channels, etc.) can be varied for optimal quantification of trauma measurement.

The measured electrical resistivity of a liquid gage element is determined by the deformation and geometry change of the surrounding elastomer. Some exemplary conductive liquids include ionic liquids, aqueous solutions, and liquid metal as outlined in Table 1.

TABLE 1

Properties of conductive liquids

| Type | Liquid | Resistivity (Ω mm) | Melting Point (° C.) |
|---|---|---|---|
| Ionic Liquids | 1-Ethyl-3-methylimidazolium bis(trifluoromethylsulfonyl)imide | ~1,136 [3] | −17 |
| | 1-Ethyl-3-Methylimidazolium Acetate | ~3571 [3] | <−20 |
| Aqueous Solution | 2.7 Mol NaCl in 1:1 vol % of DI water and Glycerol | 63.7 | N/A |
| Liquid Metals | Eutectic-Gallium-Indium (75,5% Ga, 24.5% In by weight) | $29.4 \times 10^{-5}$ | 15.7 |
| | Eutectic-Gallium-Indium-Tin (68.5% Ga, 21.5% In, 10% Sn by weight) | $28.9 \times 10^{-5}$ | −19 |

Comparative testing of the conductive liquids was performed by filling silicon tubing (Platinum-Cured Silicon Tubing, Cole-Parmer) with inner diameter of 0.012". Tube lengths of 100 mm were filled with the respective liquids, 30 gage Copper wire was inserted into each end, and a silicon sealant (Silpoxy, Smooth-On) was used to encapsulate the ends. The use of ionic liquids generated starting resistances on the order of $1.5 \times 10^6$-$5 \times 10^6 \Omega$. The ionic liquids initially resulted in operable sensors but as time went on (days later), subsequent testing showed drastically different resistance values. This was determined to be the result of a reaction between the copper test leads and the ionic liquids. This instability and the toxicity of the ionic liquids deemed them a poor choice. The aqueous solution of sodium chloride mixed with 1:1 vol. % DI water and glycerol resulted in a starting resistance of ~87,000Ω. The addition of glycerol provided greater viscosity to the solution which better matched the impedance of the surrounding elastomer matrix. The initially operable sensors, however, lost continuity after a few days as both air bubbles and precipitates of NaCl crystals formed in the tube. Above 1.23 volts, electrolysis of water divides molecules to produce hydrogen and oxygen which renders the sensor non-functional. Liquid metals have garnered interest as they are flexible and can provide a functional element over any range of stretch that the surrounding elastomer matrix can attain. Both eutectic-GaIn and eutectic-GaInSn (Galinstan) have similar conductivity properties, however the addition of Sn reduces the melting point from 15.7 to −19° C. For the purposes of this research, eutectic-GaIn was chosen for its availability and low cost. The ionic liquid resulted in an initial resistance of 0.40Ω when filled in the 100 mm length of silicon tubing. While many think that liquid metals are toxic (as a result of liquid metals being associated with Mercury), e-GaIn has low toxicity. Unlike the other liquids tested, the e-GaIn test sensor showed long-term stability over time.

The primary factors in choosing an elastomer for embedding a liquid metal element are ability to stretch and deform without fracture and hardness for impedance matching to the application. Previous research has utilized elastomers, the most common of which are Polydimethylsiloxane (PDMS) and platinum-cure silicones to make up the bodies of the soft sensors. The typical properties are listed in Table 2.

TABLE 2

Properties of Elastomeric Materials

| Material | Material Class | Elongation at break | Tensile Strength (MPa) | Shore Hardness | Working Time (minutes) |
|---|---|---|---|---|---|
| Sylgard 184 [1] | PDMS | ~160% [2] | 6.7 | 43 | 90 |
| Smooth-Sil 950 [3] | Platinum-Cure Silicone | 320% | 2.17 | 50A | 45 |
| EcoFlex 00-30 [4] | Platinum-Cure Silicone | 900% | 1.38 | 00-30 | 45 |

Based on these properties, mainly the elongation and ability to conform due to its soft nature, EcoFlex 00-30 (available from Smooth-On, Inc., Macungie, PA) was chosen as an exemplary elastomer for the gage matrix. Sil-Poxy (Smooth-On Inc.), a single component adhesive for bonding platinum-cure silicone to itself and other objects, was purchased to seal the liquid metal gage-elements where they interfaced with the test leads.

It should be noted that, unlike traditional metal strain gages that have standard initial resistances of 120 or 350Ω and a known gage factor calibration, custom made soft strain sensors with a liquid metal sensing element have much lower initial resistances (<10Ω) The low resistances make the error due to test lead resistance and contact resistance amplified.

One of the challenges associated with soft elastomeric sensors is the impedance mismatch at the interface between the soft liquid metal sensor element and the copper wire test leads. To combat this issue, conductive thread (e.g, Liberator 40, Syscom Advanced Materials, Columbus, OH) may be used in some circumstances. The thread is composed of a high-strength Vectran fiber core with a conductive metal outer layer. It is 72% lighter than the 30 gage copper wire used in other gages with 5 times the break strength. Composed of 40 filaments that are twisted at 4.5 twists/inch, the thread provided a flexible electrical path that won't impede the gage's ability to conform to complex movements. A gage with channels fabricated by casting tape on Si wafer was assembled in the same manner as other gages, however instead of inserting copper wires, the conductive thread was used. Inserting the thread was in itself a challenge. Unlike the copper wire which is stiff enough to follow the paths left by syringes, the thread is light-weight and flexible. To insert the thread, a small knot was tied at one end and a syringe was used to push the thread through the paths left by the syringes used for filling the liquid metal. A uniaxial stretch test (5 cycles) was performed. The initial zero-strain resistance (2.627Ω) was similar to other gages with channels formed using the same method.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method comprising:
providing at least one sensor comprising a channel and a pair of test leads, the channel comprising channel ends, the pair of test leads being connected to said channel ends; and an elastomer encasing the at least one sensor such that the test leads extend from the elastomer, the at least one sensor comprising a plurality of pressure sensors,
embedding the at least one sensor and the elastomer in a biofidelic human tissue, the elastomer being mechanically impedance-matched to the biofidelic human tissue, wherein said embedding the at least one sensor and the elastomer in a biofidelic human tissue comprises distributing the plurality of pressure sensors along an axis with known distances therebetween in the biofidelic human tissue,
applying a constant current to the at least one sensor;
subjecting the biofidelic human tissue to one of an impact and a blast;
measuring the one of the impact and the blast as a change in voltage in the at least one sensor;
converting the change in voltage to pressure on the biofidelic human tissue, and
calculating a pressure wave speed in the biofidelic human tissue of the one of the impact and the blast using time of flight between the distributed plurality of pressure sensors, the pressure on the biofidelic human tissue, and the known distances between the distributed plurality of pressure sensors.

2. The method of claim 1, wherein the at least one sensor comprises a plurality of strain sensors,
wherein said method further comprises:
converting the change in voltage to strain on the biofidelic human tissue.

3. The method of claim 1,
wherein the channel comprises one of a rectilinear channel and a spiral channel.

4. The method according to claim 1, wherein the biofidelic human tissue comprises biofidelic brain tissue.

5. A method comprising:
providing at least one sensor comprising a channel and a pair of test leads, the channel comprising channel ends, the pair of test leads being connected to said channel ends; and an elastomer encasing the at least one sensor such that the test leads extend from the elastomer, the at least one sensor comprising a plurality of pressure sensors,
embedding the at least one sensor and the elastomer in a biofidelic human tissue, the elastomer being mechanically impedance-matched to the biofidelic human tissue, wherein said embedding the at least one sensor and the elastomer in a biofidelic human tissue comprises distributing the plurality of pressure sensors in a cubic orientation in the biofidelic human tissue,
applying a constant current to the at least one sensor;
subjecting the biofidelic human tissue to one of an impact and a blast;
measuring the one of the impact and the blast as a change in voltage in the at least one sensor; and
calculating a pressure wave speed in the biofidelic human tissue in three dimensions of the one of the impact and the blast using time of flight between the distributed plurality of pressure sensors, the pressure on the biofidelic human tissue, and the known distances between the distributed plurality of pressure sensors.

6. The method according to claim 5, wherein the biofidelic human tissue comprises biofidelic brain tissue.

7. The method of claim 5, wherein the at least one sensor comprises a plurality of strain sensors arranged in a cubic orientation,
wherein said method further comprises:
converting the change in voltage in the plurality of strain sensors to volumetric strain on the biofidelic human tissue.

8. The method of claim 5, wherein the channel comprises one of a rectilinear channel and a spiral channel.

* * * * *